(12) United States Patent
Viola

(10) Patent No.: US 9,788,884 B2
(45) Date of Patent: *Oct. 17, 2017

(54) SURGICAL INSTRUMENT INCLUDING INDUCTIVELY COUPLED ACCESSORY

(71) Applicant: Covidien LP, Mansfield, MA (US)

(72) Inventor: Frank J. Viola, Sandy Hook, CT (US)

(73) Assignee: Covidien LP, Mansfield, MA (US)

(*) Notice: Subject to any disclaimer, the term of this patent is extended or adjusted under 35 U.S.C. 154(b) by 575 days.

This patent is subject to a terminal disclaimer.

(21) Appl. No.: 14/072,033

(22) Filed: Nov. 5, 2013

(65) Prior Publication Data

US 2014/0052129 A1 Feb. 20, 2014

Related U.S. Application Data

(63) Continuation of application No. 13/329,981, filed on Dec. 19, 2011, now Pat. No. 8,603,089.

(60) Provisional application No. 61/434,007, filed on Jan. 19, 2011.

(51) Int. Cl.
A61B 18/12 (2006.01)
A61B 17/00 (2006.01)
A61B 18/14 (2006.01)
A61B 90/30 (2016.01)
A61B 90/00 (2016.01)

(52) U.S. Cl.
CPC .... *A61B 18/1206* (2013.01); *A61B 17/00234* (2013.01); *A61B 18/1445* (2013.01); *A61B 90/30* (2016.02); *A61B 90/361* (2016.02); *A61B 2017/00411* (2013.01); *A61B 2017/00415* (2013.01); *A61B 2017/00734* (2013.01)

(58) Field of Classification Search
CPC .......... A61B 18/1206; A61B 17/00234; A61B 18/1445; A61B 90/30; A61B 90/361; A61B 2017/00411; A61B 2017/00415; A61B 2017/00734
USPC ...................... 606/1, 27–52; 607/96–99, 103
See application file for complete search history.

(56) References Cited

U.S. PATENT DOCUMENTS

| 5,369,251 A | 11/1994 | King et al. |
| 5,849,020 A | 12/1998 | Long et al. |
| 6,676,660 B2 | 1/2004 | Wampler et al. |
| 7,588,565 B2 | 9/2009 | Marchitto et al. |
| 7,900,805 B2 | 3/2011 | Shelton, IV et al. |
| 7,967,839 B2 | 6/2011 | Flock et al. |

(Continued)

FOREIGN PATENT DOCUMENTS

| EP | 1055400 | 11/2000 |
| EP | 1330991 | 7/2003 |
| WO | 02/058544 | 8/2002 |

OTHER PUBLICATIONS

European Search Report for EP 12151495 dated May 20, 2015.

*Primary Examiner* — Christopher A Flory
*Assistant Examiner* — Jonathan Kuo

(57) ABSTRACT

A surgical instrument system includes a surgical instrument, a power supply, and an accessory. The surgical instrument has a first induction device positioned therein. The accessory is selectively operably couplable to the surgical instrument. The accessory includes a second induction device that is inductively coupled with the first induction device when the accessory is operably coupled to the surgical instrument such that the power supply provides power to the accessory.

19 Claims, 4 Drawing Sheets

(56) References Cited

U.S. PATENT DOCUMENTS

| | | | |
|---|---|---|---|
| 8,597,295 B2 * | 12/2013 | Kerr | A61B 18/1402 606/51 |
| 8,603,089 B2 | 12/2013 | Viola | |
| 2002/0107517 A1 | 8/2002 | Witt et al. | |
| 2002/0111624 A1 | 8/2002 | Witt et al. | |
| 2003/0139742 A1 | 7/2003 | Wampler et al. | |
| 2003/0236518 A1 | 12/2003 | Marchitto et al. | |
| 2004/0210282 A1 | 10/2004 | Flock et al. | |
| 2005/0004569 A1 | 1/2005 | Witt et al. | |
| 2005/0092738 A1 * | 5/2005 | Ring | B29C 66/21 219/600 |
| 2007/0129716 A1 | 6/2007 | Daw et al. | |
| 2009/0062739 A1 | 3/2009 | Anderson | |
| 2009/0271998 A1 * | 11/2009 | Carlen | G01D 18/00 33/706 |
| 2009/0326527 A1 | 12/2009 | Ocel et al. | |
| 2011/0251606 A1 * | 10/2011 | Kerr | A61B 18/1402 606/34 |
| 2012/0116368 A1 * | 5/2012 | Viola | A61B 17/00234 606/1 |
| 2012/0116369 A1 * | 5/2012 | Viola | A61B 17/00234 606/1 |

* cited by examiner

SURGICAL INSTRUMENT INCLUDING INDUCTIVELY COUPLED ACCESSORY

CROSS-REFERENCE TO RELATED APPLICATIONS

This application is a continuation of U.S. patent application Ser. No. 13/329,981 filed Dec. 19, 2011, now U.S. Pat. No. 8,603,089, which claims benefit of U.S. Provisional Application No. 61/434,007 filed Jan. 19, 2011, and the disclosures of each of the above-identified applications are hereby incorporated by reference in their entirety.

BACKGROUND

Technical field

This application relates to surgical instruments and more particularly, to energy sources for use with surgical instrument accessories.

Background of the Related Art

A typical surgery employs a plurality of different surgical instruments and accessory devices for use with the various surgical instruments. When attaching accessory devices, e.g., illumination devices or cameras, there is often a need to satisfy the energy needs of the accessory device. While self contained energy sources like batteries are often utilized, they take up valuable space in the accessory device and often have limited energy storage capacity. As such, removal or repositioning of the accessory may be necessary to change a battery or other energy storage device, which, if required during surgery or other medical procedure, can inhibit efficiency.

SUMMARY

Accordingly, the present disclosure is directed to a surgical instrument system including a surgical instrument, a power supply, and an accessory. The surgical instrument has a first induction device positioned therein. The power supply is electrically coupled to the surgical instrument. The accessory is selectively operably couplable to the surgical instrument such that the power supply provides power to the accessory.

The first induction device and the second induction device may be positioned adjacent one another. In some embodiments, the first induction device and the second induction device are concentrically aligned.

The first induction device can include a first electrical conduit that is electrically coupled to a second power supply and the second induction device can include a second electrical conduit that is inductively coupled to the first electrical conduit of the first induction device. One or both of the first electrical conduit and second electrical conduit can include one or more wires that are at least partially wound a predetermined number of windings about the respective first and second induction devices. The one or more wires can produce a voltage output when the second power supply is electrically coupled to the first induction device, wherein the amount of voltage output increases as the number of windings of the one or more wires increases.

In one embodiment, one or both of the first and second induction devices includes a spool about which at least a portion of the one or more wires are wound. In another embodiment, one or both of the first and second induction devices include a pole member about which at least a portion of the one or more wires are wound.

In some embodiments, an instrument power supply is electrically coupled to the first induction device.

One or more of the power supplies may be positioned within the surgical instrument. One or both of the power supplies may produce alternating current and/or direct current. One or both of the power supplies may include one or more batteries.

The second induction device is inductively coupled with the first induction device when the accessory is operably coupled to the surgical instrument such that only the instrument power supply provides power to the accessory. The accessory in some embodiments includes a housing that defines a channel therethrough and the surgical instrument includes a shaft, the channel configured to accommodate at least a portion of the shaft. The accessory may include a powering device that includes one or more of a camera, a sensor, and an illumination device. The powering device can be inductively powered by the accessory power supply when the accessory is operably coupled to the surgical instrument. The accessory may include a converter (e.g., rectifier) that converts the alternating current into direct current.

The accessory power supply can be internal or external of the instrument.

BRIEF DESCRIPTION OF THE DRAWINGS

Various embodiments of the present disclosure are described herein with reference to the drawings wherein.

DETAILED DESCRIPTION

Figure 1:
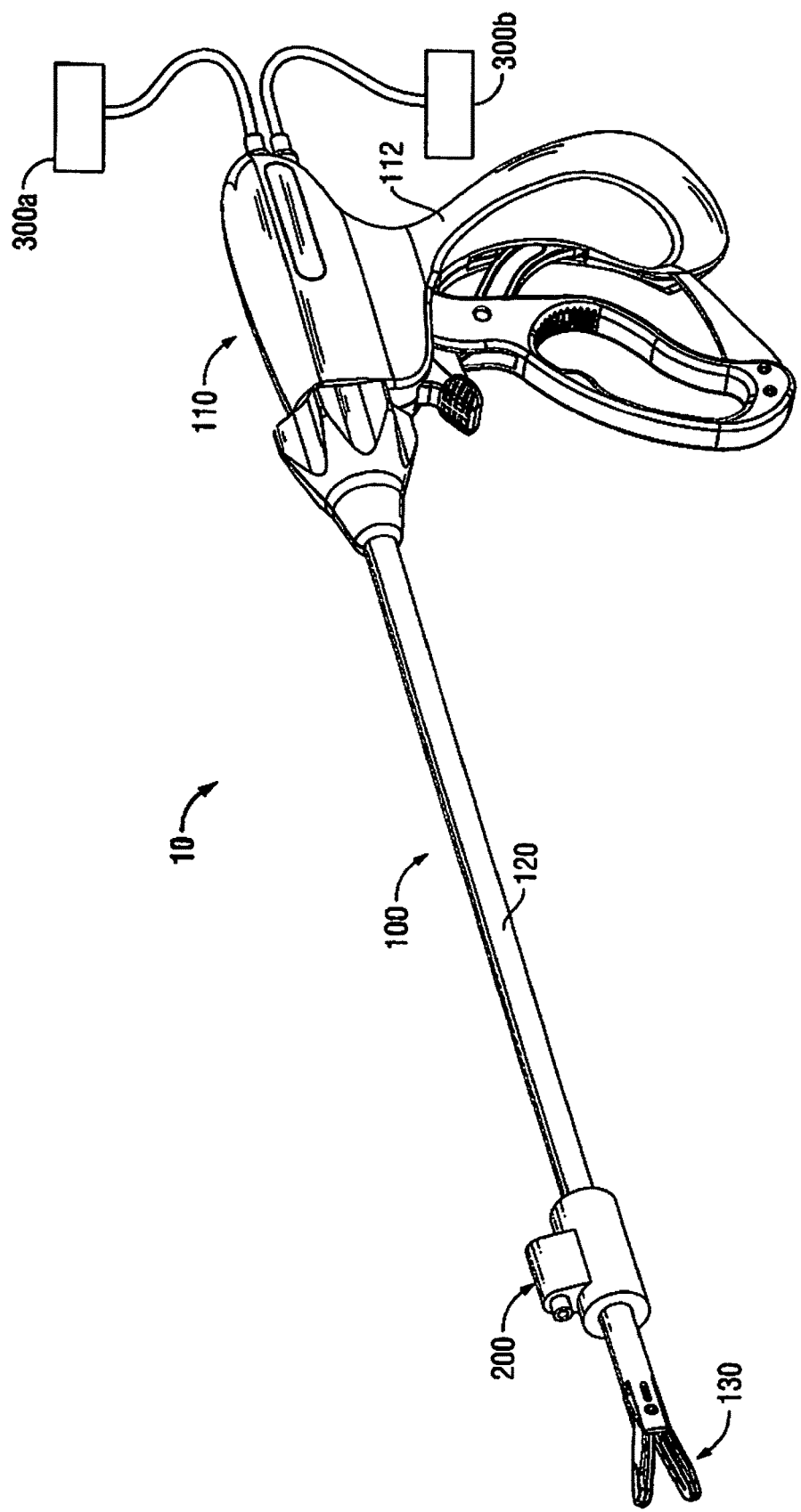
FIG. 1 is a perspective view of one embodiment of a surgical instrument system in accordance with the present disclosure.

Embodiments of the presently disclosed surgical instrument system are described in detail with reference to the drawings, wherein like reference numerals designate similar or identical elements in each of the several views. However, the disclosed embodiments are merely examples of the disclosure, which may be embodied in various forms. In the drawings and the description that follows, the term "proximal" refers to the end of the surgical instrument system that is closer to the user, whereas the term "distal" refers to the end of the surgical instrument system that is further from the user.

Figure 2:
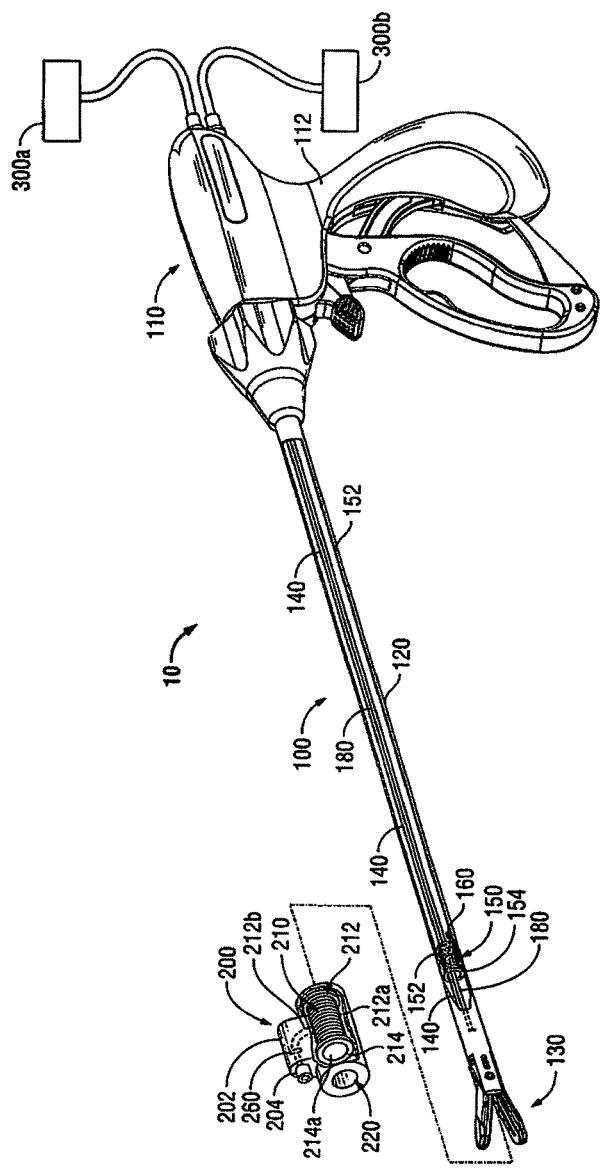
FIG. 2 is a perspective view, with parts separated, of the surgical instrument and the accessory of the surgical instrument system of FIG. 1, each of the surgical instrument and the accessory having a portion thereof removed for clarity.

Referring now to the drawings, FIGS. 1 and 2 illustrate one embodiment of a surgical instrument system 10. The surgical instrument system 10 includes a surgical instrument 100, an accessory 200 selectively operably couplable to the surgical instrument 100, a first power supply 300a, and a second power supply 300b. The first and second power supplies 300a, 300b may be any suitable power source including one or more electrical generators and/or one or more batteries. In addition, one or both of the first and second power supplies 300*a*, 300*b* may be positioned internally or externally of the surgical instrument 100. The first power supply 300*a* is electrically coupled to the surgical instrument 100 to provide power only to the surgical instrument 100 without providing power to the accessory 200. The second power supply 300*b* is electrically coupled to a first induction device 150 that is positioned within the surgical instrument 100 so that when the accessory 200 is operably coupled to the surgical instrument 100, the second power supply 300*b* only powers the accessory 200 via inductive coupling without providing power to the other components of the surgical instrument 100. However, in some embodiments, either the first or second power supply 300*a*, 300*b* may provide power to both the surgical instrument 100 and the accessory 200. As such, only one of the first and second power supplies 300*a*, 300*b* may be electrically coupled with the surgical instrument 100 and the accessory 200 in certain embodiments.

Figure 1A:
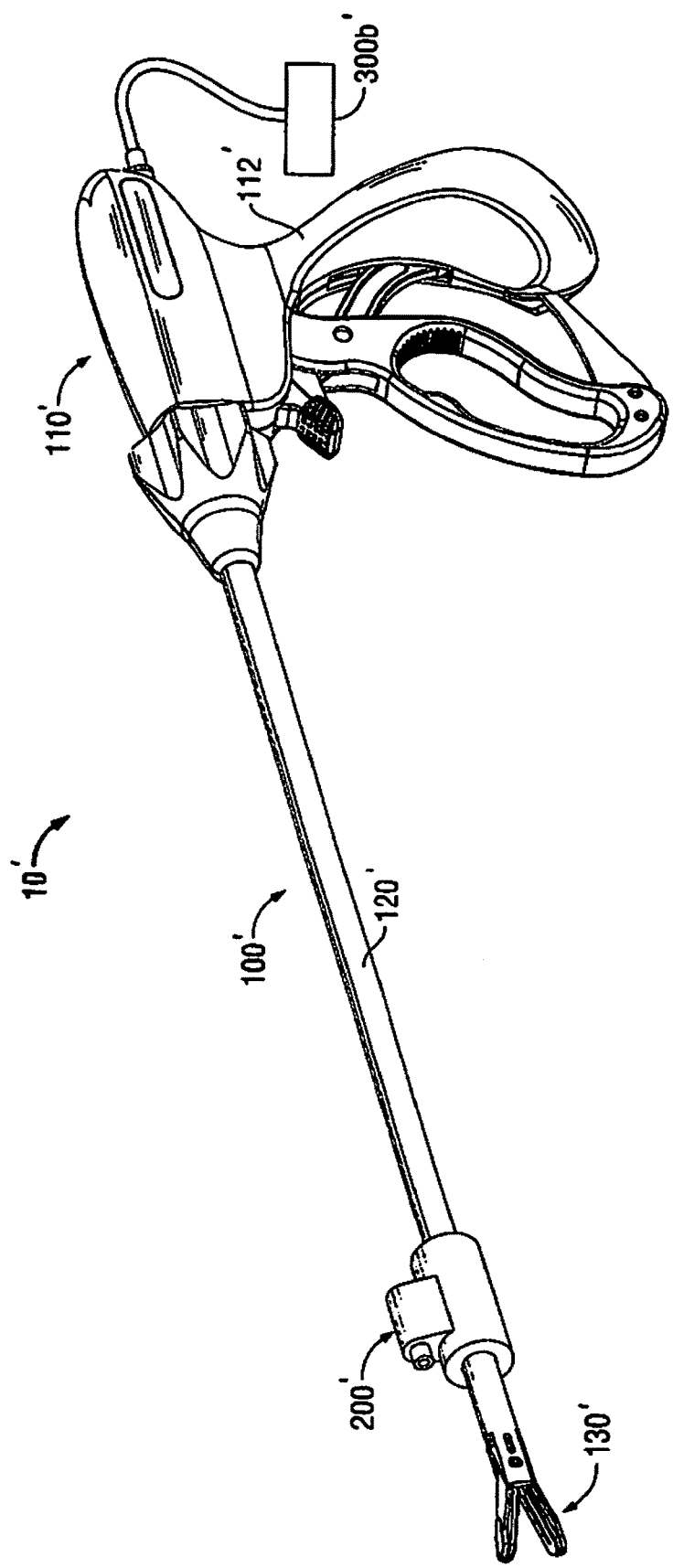
FIG. 1A is a perspective view of another alternate embodiment of a surgical instrument system in accordance with the present disclosure.

In the alternate embodiment of FIG. 1A, the instrument itself is not powered and therefore a power supply for the instrument is not provided. In all other respects, instrument 10' is identical to instrument 10 of FIG. 1 and the parts are labeled with "prime" designations. Consequently, the description of the components of FIG. 1 is applicable to FIG. 1A except for the absence of power supply 300*a*.

The surgical instrument 100 (and 100') includes a housing 110, an elongated shaft 120, a tool assembly 130, one or more electrical conduits 140, and a first induction device 150 (FIG. 2). The shaft 120 extends from the distal end of the housing 110. The tool assembly 130 is operably coupled to the distal end of the shaft 120. The tool assembly 130 may be remotely operable for the handle assembly via a drive assembly 180 that is operably coupled to one or more handles 112 of the housing 110. The drive assembly 180 may be positioned within one or both of the housing 110 and the shaft 120. In this respect, the tool assembly 130 may be operable remotely from the handle assembly via the drive assembly 180 to engage tissue upon the actuation of the one or more handles 112 of the housing 110.

One or more electrical conduits 140 (e.g., one or more wires or cables) are positioned within one or more of the housing 110, the shaft 120, and the tool assembly 130. As best illustrated in FIG. 2, the distal end of the one or more electrical conduits 140 may be electrically coupled to the tool assembly 130 while the proximal end of the one or more electrical conduits 140 may be electrically coupled to the first power supply 300*a*. As shown in FIG. 2, the one or more electrical conduits 140 may extend through the shaft 120 and housing 110. In this manner, the one or more electrical conduits 140 may provide power, e.g., electricity in the form of alternating current, direct current, an AC signal superimposed on a DC signal (which enables powering both the instrument and accessory utilizing only two wires) and/or pulsating DC current, as well as other waveforms such as saw tooth, to each of the components of the surgical instrument 100 without providing power to the first induction device 150. In the embodiment of FIG. 1A where the tool assembly is not powered, electrical conduits 140 need not be provided.

As best shown in FIG. 2, the first induction device 150, which can be utilized in the same way with instruments 100 or 100' but for brevity is described only with use with instrument 100 of FIG. 1, is shown positioned within the shaft 120 but may also be positioned within the housing 110 and/or the tool assembly 130. When the first induction device 150 is positioned within the housing 110 or the tool assembly 130, the accessory 200 can also be positioned adjacent the housing 110, the tool assembly 130, and/or the shaft 110. The first induction device 150 includes one or more electrical conduits 152 (e.g., one or more wires or cables such as copper wire or any other suitable material capable of transmitting electric current). At least a portion of length of the electrical conduits 152 of the first induction device 150 may extend proximally through the shaft 120 and the housing 110 and electrically couple with the second power supply 300*b*. In addition, the first induction device 150 includes a spool 154 about which the one or more electrical conduits 152 are at least partially wound a predetermined number of windings. When the first induction device 150 is in electrical communication with the second power supply 300*b*, the one or more electrical conduits 152 become electrically charged (e.g., via alternating and/or direct current and/or an AC signal superimposed on a DC signal) so that an electric field (not shown) is formed around the first induction device 150. In this manner, the one or more electrical conduits 152 produce a voltage output that corresponds to the number of windings about the spool 154 when the second power supply 300*b* is electrically coupled to the first induction device 150. In particular, the amount of voltage output changes as the ratio between the number of turns of each winding of the one or more electrical conduits 152 changes. As best illustrated in FIG. 2, one or more converters 160 that convert alternating current into direct current and/or direct current into alternating current may be operably coupled to the first induction device 150.

The accessory 200, which is mountable to instrument 100 or 100', includes a housing 202, one or more powered devices 204 (e.g., including cameras, sensors, illumination devices, or any other suitable powered devices that could assist the clinician in performing a medical/surgical procedure) and a second induction device 210. The one or more powered devices 204 and the second induction device 210 are coupled to the housing 202. The second induction device 210 is configured and dimensioned to inductively couple with the first induction device 150 when the accessory 200 is operably coupled to the surgical instrument 100 such that the electric field formed around the first induction device 150 solely powers the accessory 200. In particular, the second induction device 210 includes one or more electrical conduits 212 (e.g., one or more wires or cables such as copper wire or any other suitable material capable of transmitting electric current). A first portion 212*a* of the length of the one or more electrical conduits 212 is wound about a spool 214 positioned within the housing 202. The spool 214 defines a passage 214*a* therethrough. A second portion 212*b* of the length of the one or more electrical conduits 212 is coupled to the one or more powered devices 204. In this respect, the electric field formed around the first induction device 150 generates electric current in the one or more electrical conduits 212 of the second induction device 210 which powers the powered devices 204. The housing 202 may define an opening or channel 220 therethrough that may accommodate at least a portion of the shaft 120 so that the accessory 200 may be operably coupled to the surgical instrument 100. As shown in FIG. 2, one or more converters 260 that convert alternating current into direct current (e.g. rectifiers) and/or direct current into alternating current (e.g. inverters) may be operably coupled to the second induction device 210.

As an alternative to opening 220, the accessory can have a U or C-shape to clamp onto the shaft 120 (or 120') as the gap in the U or C would be pressed onto the shaft for frictional engagement so the induction devices are adjacent.

In some embodiments, the first induction device 150 and the second induction device 210 may be positioned adjacent and/or offset from one another. In some embodiments, the first induction device 150 and the second induction device 210 may be concentrically aligned.

Figure 3:
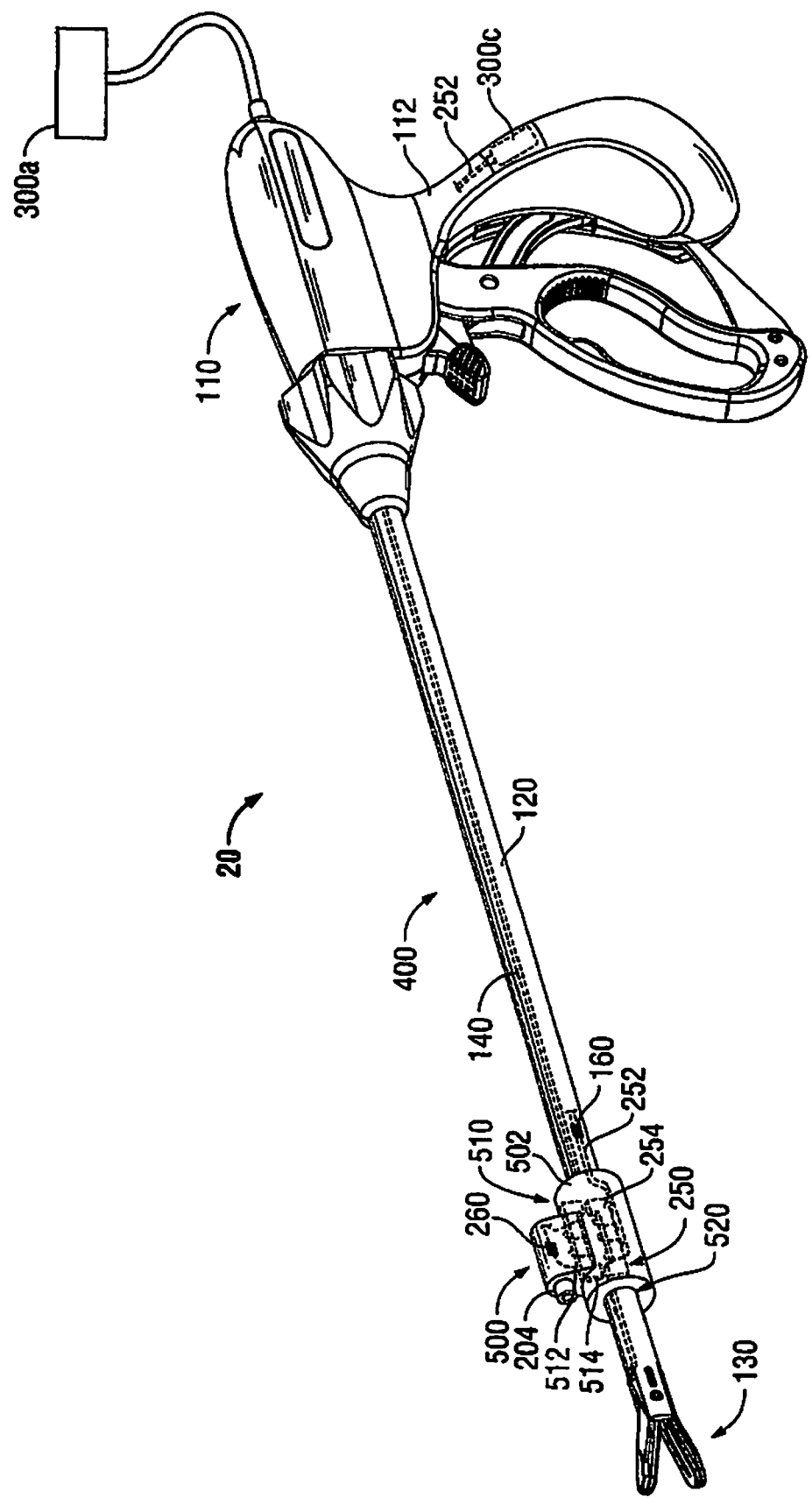
FIG. 3 is a perspective view of yet another embodiment of a surgical instrument system having another embodiment of a surgical instrument and another embodiment of an accessory, each of the surgical instrument and the accessory having a portion thereof removed for clarity.

Referring now to FIG. 3, another embodiment of a surgical instrument system is generally referred to as 20. The surgical instrument system 20 is similar to surgical instrument system 10 and is described below to the extent necessary to describe the differences in the structure and operation thereof. The surgical instrument system 20 includes a surgical instrument 400, an accessory 500 selectively operably couplable to the surgical instrument 400, a first power supply 300a, and a second power supply 300c. The first power supply 300a is electrically coupled to the surgical instrument 400 to provide power only to the surgical instrument 400 without providing power to the accessory 500. The second power supply 300c is electrically coupled to a first induction device 250 that is positioned within the surgical instrument 400 so that the second power supply 300c only powers the accessory 500 via inductive coupling without providing power to the surgical instrument 400. The second power supply 300c is positioned internal of the instrument, e.g. in housing 110. In alternate embodiments, either the first or second power supply 300a, 300c may provide power to both the surgical instrument 400 and the accessory 500. In this manner, only one of the first and second power supplies 300a, 300c may be electrically coupled with the surgical instrument 400 and the accessory 500. It is also contemplated that only power supply 300c, positioned internal of the instrument, is provided for powering the accessory, and the tool assembly is manually actuated rather than powered.

The surgical instrument 400 includes a housing 110, a shaft 120, a tool assembly 130, one or more electrical conduits 140, and a first induction device 250. The first induction device 250 is positioned within the shaft 120 but may be positioned within one or more of the housing 110, the shaft 120, and the tool assembly 130. The first induction device 250 includes one or more electrical conduits 252 (e.g., one or more wires or cables such as copper wire or any other suitable material capable of transmitting electric current) that are at least partially wound about a pole member 254 of the first induction device 250. At least a portion of length of the electrical conduits 252 of the first induction device 250 may extend proximally through the shaft 120 and electrically couple with the second power supply 300c.

When the first induction device 250 is in electrical communication with the second power supply 300c, the one or more electrical conduits 252 become electrically charged (via direct or alternating current) so that an electric field is formed around the first induction device 250. As best illustrated in FIG. 3, one or more converters 160 that convert alternating current into direct current and/or direct current into alternating current may be operably coupled to the first induction device 250.

The accessory 500 includes a housing 502, one or more powered devices 204 (e.g., including cameras, sensors, illumination devices, or any other suitable powered devices that could assist the clinician in performing a medical/surgical procedure) and a second induction device 510. The one or more powered devices 204 and the second induction device 510 are coupled to the housing 502. The second induction device 510 is configured and dimensioned to inductively couple with the first induction device 250 when the accessory 500 is operably coupled to the surgical instrument 400 such that the electric field formed around the first induction device 250 solely powers the accessory 500. In particular, the second induction device 510 includes one or more electrical conduits 512 (e.g., one or more wires or cables such as copper wire or any other suitable material capable of transmitting electric current). A portion of the length of the one or more electrical conduits 512 are wound about a pole member 514 positioned within the housing 502. Another portion of the length of the one or more electrical conduits 512 is coupled to the one or more powered devices 204. In this respect, the electric field (not shown) formed around the first induction device 250 generates electric current in the one or more electrical conduits 512 of the second induction device 510 which powers the powered devices 204. As best illustrated in FIG. 3, one or more converters 260 that convert alternating current into direct current and/or direct current into alternating current may be operably coupled to the second induction device 510. The housing 502 may define a channel 520 therethrough that may accommodate at least a portion of the shaft 120 so that the accessory 500 may be operably coupled to the surgical instrument 400. Alternately, the housing 502 may have a U or C-shape to clamp onto the shaft 120.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument system, comprising:
a surgical instrument including a shaft supporting a first induction device; and
an accessory having a housing that defines a channel configured to accommodate at least a portion of the shaft and removably couple the accessory to the shaft, the accessory including a second induction device, the second induction device inductively coupling to the first induction device as the accessory is coupled to the shaft to power the accessory.

2. The surgical instrument system according to claim 1, wherein the first induction device includes an electrical conduit that is electrically coupled to a power supply and the second induction device includes an electrical conduit that is inductively coupled to the electrical conduit of the first induction device.

3. The surgical instrument system according to claim 2, wherein at least one of the electrical conduits includes at least one wire that is at least partially wound a predetermined number of windings about a respective one of the first and second induction devices.

4. The surgical instrument system according to claim 3, wherein at least one of the first and second induction devices includes a spool about which at least a portion of the at least one wire is wound.

5. The surgical instrument system according to claim 3, wherein at least one of the first and second induction devices includes a pole member about which at least a portion of the at least one wire is wound.

6. The surgical instrument system according to claim 3, wherein the at least one wire produces an electrical output when the power supply is electrically coupled to the first induction device.

7. The surgical instrument system according to claim 1, wherein the first induction device and the second induction device are concentrically aligned.

8. The surgical instrument system according to claim 1, wherein the accessory includes at least one of a camera, a sensor, and an illumination device that is powered by inductively coupling the first and second induction devices.

9. The surgical instrument system according to claim 1, wherein the first induction device and the second induction device are positioned adjacent to one another.

10. A surgical instrument system, comprising:
- a surgical instrument including a shaft extending therefrom, the shaft supporting an end effector and a first induction device;
- an accessory selectively removably coupled to the shaft, the accessory including a second induction device that is inductively coupled to the first induction device when the accessory is coupled to the shaft; and
- a first power supply electrically coupled to the first induction device;
- a second power supply coupled to the surgical instrument for powering at least the end effector thereof.

11. The surgical instrument system according to claim 10, wherein the first power supply solely powers the accessory and the second power supply solely powers the end effector.

12. The surgical instrument system according to claim 10, wherein at least one of the first and second power supplies is positioned within the surgical instrument.

13. The surgical instrument system according to claim 10, wherein at least one of the first and second power supplies produces alternating current.

14. The surgical instrument system according to claim 13, wherein the accessory includes a converter that converts the alternating current into direct current.

15. The surgical instrument system according to claim 10, wherein at least one of the first and second power supplies includes at least one battery.

16. The surgical instrument system according to claim 10, wherein at least one of the first and second power supplies is external of the surgical instrument.

17. The surgical instrument system according to claim 10, wherein the accessory includes at least one of a camera, a sensor, and an illumination device that is powered by inductively coupling the first and second induction devices.

18. The surgical instrument system according to claim 10, wherein the first induction device and the second induction device are concentrically aligned when the accessory is coupled to the surgical instrument.

19. The surgical instrument system according to claim 10, wherein the first induction device includes a first electrical conduit and the second induction device includes a second electrical conduit, wherein at least one of the first electrical conduit and second electrical conduit includes at least one wire that is at least partially wound a predetermined number of windings about a respective one of the first and second induction devices.

* * * * *